Figure 3:
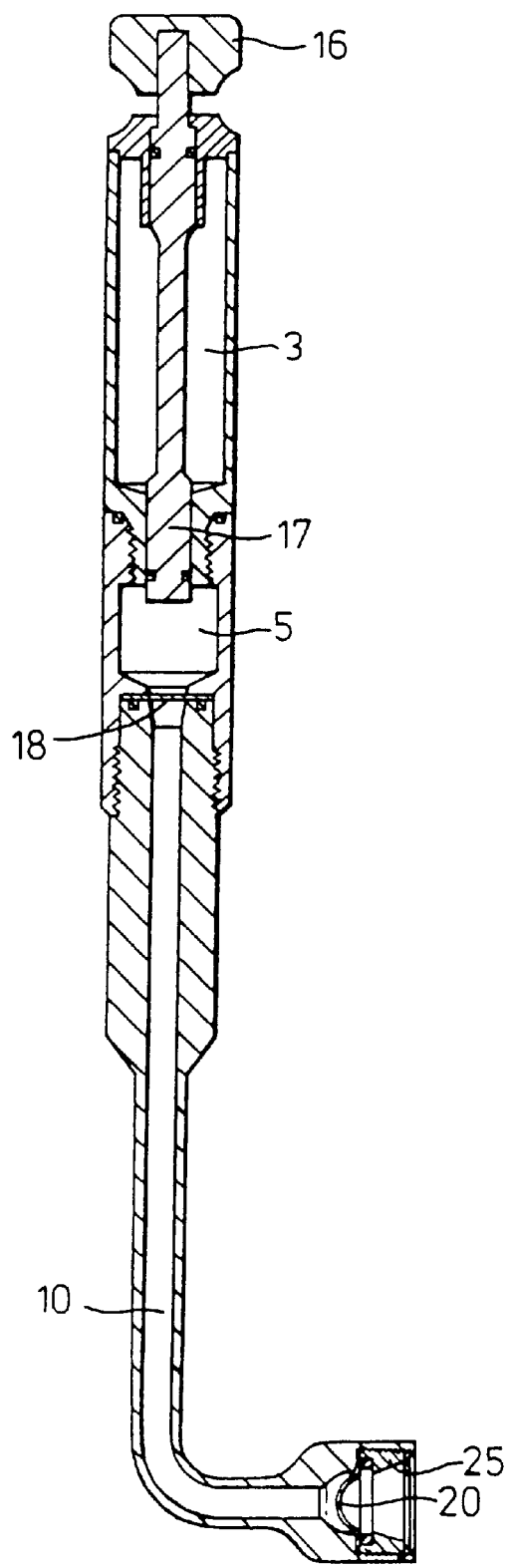

United States Patent [19]
Bellhouse et al.

[11] Patent Number: 6,010,478
[45] Date of Patent: Jan. 4, 2000

[54] TRANS-MUCOSAL PARTICLE DELIVERY

[75] Inventors: Brian John Bellhouse; John Bell, both of Islip; John Christopher Greenford, Abingdon; David Francis Sarphie, Witney, all of United Kingdom

[73] Assignee: PowderJect Research Limited, United Kingdom

[21] Appl. No.: 08/919,184

[22] Filed: Aug. 14, 1997

Related U.S. Application Data

[63] Continuation-in-part of application No. PCT/GB96/00340, Feb. 14, 1996.

[30] Foreign Application Priority Data

Feb. 14, 1995 [GB] United Kingdom ............... 9502879

[51] Int. Cl.⁷ ................................................ A61M 5/30
[52] U.S. Cl. .......................... 604/70; 604/60; 222/631; 222/309
[58] Field of Search .................... 604/68, 70, 72, 604/131, 130, 140, 141, 143, 146; 222/631, 389

[56] References Cited

U.S. PATENT DOCUMENTS

| | | | |
|---|---|---|---|
| 3,189,029 | 6/1965 | Stephens | 604/70 |
| 3,425,413 | 2/1969 | Stephens | 604/70 |
| 3,788,315 | 1/1974 | Laurens . | |
| 4,596,556 | 6/1986 | Morrow et al. . | |
| 4,945,050 | 7/1990 | Sanford et al. . | |
| 5,049,125 | 9/1991 | Accaries et al. . | |
| 5,062,830 | 11/1991 | Dunlap . | |
| 5,064,413 | 11/1991 | McKinnon et al. | 604/72 X |
| 5,149,655 | 9/1992 | McCabe et al. . | |
| 5,204,253 | 4/1993 | Sanford et al. . | |
| 5,330,446 | 7/1994 | Weldon et al. . | |
| 5,371,015 | 12/1994 | Sanford et al. . | |
| 5,503,627 | 4/1996 | McKinnon et al. | 604/72 |
| 5,630,796 | 5/1997 | Bellhouse et al. . | |

FOREIGN PATENT DOCUMENTS

| | | |
|---|---|---|
| 0 406 778 A1 | 1/1991 | European Pat. Off. . |
| 2 360 031 | 8/1978 | France . |
| 686 344 | 1/1953 | United Kingdom . |
| WO 92/04439 | 3/1992 | WIPO . |
| WO 94/24263 | 10/1994 | WIPO . |
| WO 95/19799 | 7/1995 | WIPO . |
| WO 96/20022 | 7/1996 | WIPO . |
| WO 96/25190 | 8/1996 | WIPO . |

*Primary Examiner*—Corrine McDermott
*Assistant Examiner*—Kent Gring
*Attorney, Agent, or Firm*—Thomas P. McCracken

[57] ABSTRACT

A needleless syringe capable of accelerating particles comprising a therapeutic agent across skin or mucosal tissue of a vertebrate subject is provided. The syringe comprises an elongate tubular nozzle having a bend along its length and is connected to or capable of connection to a suitable energizing means for producing in the nozzle a supersonic condition sufficient to cause delivery of the particles to a target surface. A method for delivering particles comprising a therapeutic agent from the needleless syringe is also provided.

31 Claims, 3 Drawing Sheets

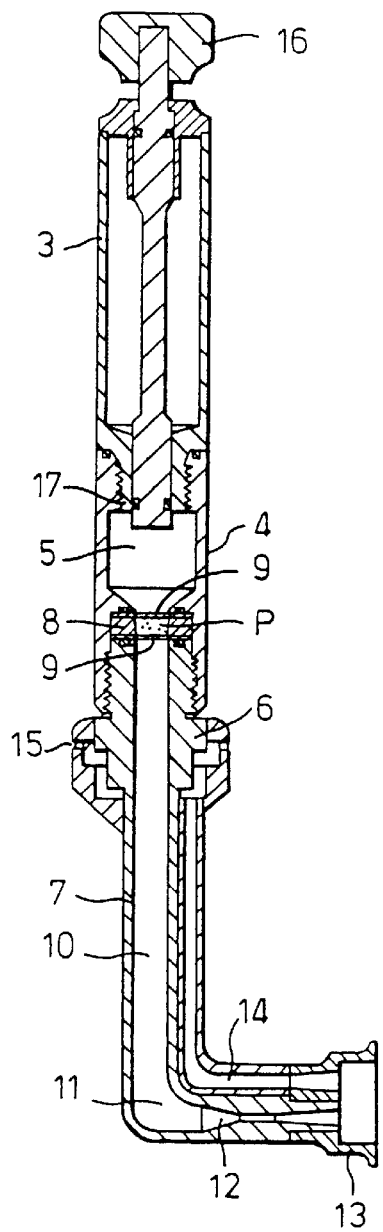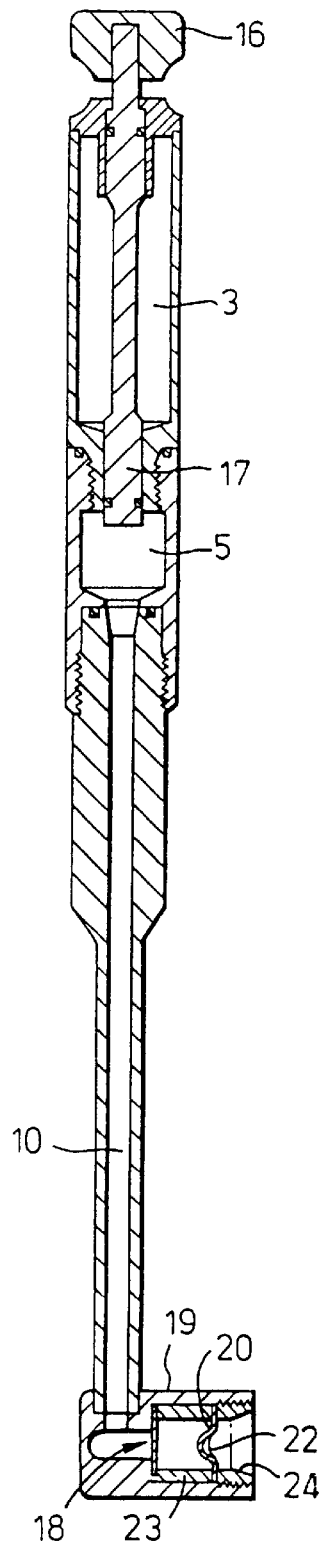

TRANS-MUCOSAL PARTICLE DELIVERY

CROSS-REFERENCE TO RELATED APPLICATION

This application is a continuation-in-part of International Patent Application Number PCT/GB96/00340, filed Feb. 14, 1996, designating the United States, from which priority is claimed pursuant to 35 U.S.C. §365(c) and which is incorporated herein by reference in its entirety.

TECHNICAL FIELD

The present invention relates generally to a needleless syringe for use in delivery of particles of a therapeutic agent to a target skin or mucosal surface.

BACKGROUND OF THE INVENTION

In commonly owned U.S. Pat. No. 5,630,796, a noninvasive delivery system is described that entails the use of a needleless syringe. The syringe is used for transdermal delivery of powdered therapeutic compounds and compositions to skin, muscle, blood or lymph. The syringe can also be used in conjunction with surgery to deliver therapeutics to organ surfaces, solid tumors and/or to surgical cavities (e.g., tumor beds or cavities after tumor resection).

The needleless syringe is constructed as an elongate tubular nozzle, having a rupturable membrane initially closing the passage through the nozzle adjacent to the upstream end of the nozzle. Particles comprising a powdered therapeutic agent are located adjacent to the membrane. The therapeutic agent is delivered using an energizing means which applies a gaseous pressure to the upstream side of the membrane that is sufficient to burst the membrane, thereby producing a supersonic gas flow through the nozzle in which the particles are entrained.

As explained in U.S. Pat. No. 5,630,796, the particles comprising the therapeutic agent may be carrier particles that have been coated, for example, with genetic material, or may be particles of powdered therapeutic agents for all kinds of therapeutic use. With respect to delivery of powdered therapeutic agents per se, e.g., agents delivered without the aid of a carrier particle, general delivery parameters include a particle size preferably in the range of about 10–40 $\mu$m, a particle density preferably in the range of about 0.5–2.0 g/cm$^3$, and an initial velocity preferably in the range of about 200–2500 m/sec with a momentum density preferably in the range of 4–7 kg/sec/m.

SUMMARY OF THE INVENTION

In one embodiment of the invention, a needleless syringe is provided. The needleless syringe is capable of accelerating particles comprising a therapeutic agent across skin or mucosal tissue of a vertebrate subject. The syringe comprises an elongate tubular nozzle having an upstream terminus and a downstream terminus and a bend between these upstream and downstream termini. The upstream terminus of the nozzle is capable of interfacing with an energizing means such as a volume of a pressurized driving gas. The syringe further includes a release means for releasing an energetic force from the energizing means into the upstream terminus of the nozzle. This energetic force creates a supersonic condition within the nozzle, e.g., a gaseous shock wave or supersonic gas flow, that is sufficient to deliver particles comprising a therapeutic agent from the syringe to target skin or mucosal tissue.

In certain aspects of the invention, the diameter of the portion of the nozzle between the bend and the downstream terminus is smaller than that of the portion of the nozzle between the upstream terminus and the bend. This configuration allows a supersonic gas flow to be attained only in the downstream portion of the nozzle, i.e., that portion between the bend and the downstream terminus, thereby avoiding the possibility of a supersonic gas flow having difficulty passing around the bend in the nozzle without a concomitant deceleration. Furthermore, the portion of the nozzle downstream from the bend can have a reduced diameter relative to that of the portion upstream of the bend to facilitate the establishment of supersonic gas flow conditions in the downstream portion of the nozzle only. It has been found that with this particular construction, a driving gas can pass through the wider upstream portion of the bend at moderate speed, before being rapidly accelerated to a supersonic speed at the narrower portion of the nozzle that is downstream of the bend. This narrower, downstream portion of the nozzle can also have a convergent portion, such as where the portion of the nozzle has a convergent/cylindrical or convergent/divergent shape, with the convergent portion of the nozzle being of greater conicity than the cylindrical or divergent portion.

In other aspects of the invention, the syringe is used to deliver particles comprising a therapeutic agent, wherein the particles are entrained in a gas flow created in the upstream portion of the nozzle and accelerated to supersonic speed as they pass through and out of the downstream portion of the nozzle for delivery to the target surface. Thus, the syringe can include upstream and downstream rupturable membranes that extend across the interior of the nozzle. Particles comprising a therapeutic agent can be housed in the nozzle between these membranes and, if the release means comprises a rupturing membrane, one of the upstream or downstream membranes can be used to initiate the supersonic condition within the nozzle to effect delivery of the particles from the syringe.

In one particular embodiment of the invention, the syringe is used to deliver particles comprising a therapeutic agent only, for example wherein the particles are not entrained within a flow of driving gas. In this embodiment, the syringe includes a diaphragm arranged over the downstream terminus of the nozzle, wherein the diaphragm has an internal surface facing the interior of the nozzle and an external surface facing outwardly from the syringe. The diaphragm is moveable between an initial position in which a concavity is provided on the external surface of the diaphragm, and a dynamic position in which the external surface of the diaphragm is substantially convex.

In certain aspects, the diaphragm is an eversible dome-shaped membrane that is comprised of a flexible polymeric material. In other aspects, the diaphragm is a bistable membrane that is moveable between an initial, inverted position and a dynamic, everted position. Particles comprising a therapeutic agent are generally housed within the concavity provided by the external surface of the diaphragm when in its initial position.

Sufficient energetic force can be imparted on the particles to be delivered from the above-described diaphragms by generating a shockwave in the portion of the nozzle that is substantially upstream of the bend and thus removed from the target surface, e.g., mucosal tissue in a patient's mouth. In this manner, the downstream portion of the nozzle can be of reduced size to facilitate positioning of the syringe within the mouth cavity.

In yet a further embodiment of the invention, a method for delivering particles comprising a therapeutic agent to a target surface is provided. The method entails providing a needleless syringe according to the invention, wherein the syringe has a nozzle with a bend between the upstream and downstream termini thereof. Once the particles have been loaded into the syringe, the downstream terminus of the nozzle is positioned adjacent to the target surface and the release means actuated to create a supersonic condition sufficient to accelerate the particles into the skin or mucosal tissue.

In certain aspects of the invention, the method is used to deliver a therapeutic agent that is a topically active local anesthetic. For example, the method can be used to deliver an anesthetic such as, but not limited to, lignocaine hydrochloride, lignocaine base, ropivacaine hydrochloride, bupivacaine, procaine, prilocaine, tetracaine, etidocaine, benzocaine, cocaine, or combinations thereof. If desired, the local anaesthetic can be mixed with epinephrine. Epinephrine (e.g., adrenaline) causes vasoconstriction in the targeted tissue, thereby helping prolong the anaesthetic effect of the local anaesthetic. In other aspects of the invention, the method is used to deliver a systemically active therapeutic agent such as, but not limited to, systemically-active organic small molecules or inorganic small molecules, peptides, proteins, vaccine compositions, oligonucleotides, and/or metal ions. Particular therapeutic agents include, for example, insulin, testosterone, growth hormones, glucagon, atropine, alprazolam, calcitonin, desmopressin, 5HT, dihydroergotamine, and interleukins.

In yet further aspects of the invention, the method is used to deliver particles comprising a therapeutic agent to a mucosal surface such as to gum mucosa, cheek mucosa, palate mucosa, vaginal mucosa, rectal mucosa, nasal mucosa, or ocular mucosa.

These and other embodiments of the present invention will readily occur to those of ordinary skill in the art in view of the disclosure herein.

BRIEF DESCRIPTION OF THE FIGURES

Some examples of syringes constructed in accordance with the present invention are illustrated in the accompanying drawings, in which:

FIG. 1 is an axial section of a first embodiment of the invention;

FIG. 2 is an axial section of a second embodiment of the invention;

FIG. 3 is an axial section of a third embodiment of the invention;

FIG. 4 is an axial section of a fourth embodiment of the invention;

FIG. 5 is a side view of a diaphragm containing particles comprising a therapeutic agent; and FIG. 6 is a side view of the diaphragm of FIG. 5 after delivery of the particles therefrom.

DETAILED DESCRIPTION OF THE PREFERRED EMBODIMENTS

Before describing the present invention in detail, it is to be understood that this invention is not limited to particular pharmaceutical formulations or process parameters as such may, of course, vary. It is also to be understood that the terminology used herein is for the purpose of describing particular embodiments of the invention only, and is not intended to be limiting.

All publications, patents and patent applications cited herein, whether supra or infra, are hereby incorporated by reference in their entirety.

It must be noted that, as used in this specification and the appended claims, the singular forms "a", "an" and "the" include plural referents unless the content clearly dictates otherwise. Thus, for example, reference to "a therapeutic agent" includes a mixture of two or more such agents, reference to "a gas" includes mixtures of two or more gases, and the like.

A. Definitions

Unless defined otherwise, all technical and scientific terms used herein have the same meaning as commonly understood by one of ordinary skill in the art to which the invention pertains. The following terms are intended to be defined as indicated below.

The term "transdermal" delivery captures both transdermal (or "percutaneous") and transmucosal administration, i.e., delivery by passage of a therapeutic agent through the skin or mucosal tissue. See, e.g., *Transdermal Drug Delivery: Developmental Issues and Research Initiatives*, Hadgraft and Guy (eds.), Marcel Dekker, Inc., (1989); *Controlled Drug Delivery: Fundamentals and Applications*, Robinson and Lee (eds.), Marcel Dekker Inc., (1987); and *Transdermal Delivery of Drugs*, Vols. 1–3, Kydonieus and Berner (eds.), CRC Press, (1987). Aspects of the invention which are described herein in the context of "transmucosal" delivery, unless otherwise specified, are meant to apply to both transdermal and transmucosal delivery. That is, the compositions, systems, and methods of the invention, unless explicitly stated otherwise, should be presumed to be equally applicable to transdermal and transmucosal modes of delivery.

As used herein, the terms "therapeutic agent" and/or "particles of a therapeutic agent" intend any compound or composition of matter which, when administered to an organism (human or nonhuman animal) induces a desired pharmacologic, immunogenic, and/or physiologic effect by local and/or systemic action. The term therefore encompasses those compounds or chemicals traditionally regarded as drugs, vaccines, prophylactics, and biopharmaceuticals including molecules such as proteins, peptides, hormones, nucleic acids, gene constructs and the like. More particularly, the term "therapeutic agent" includes compounds or compositions for use in all of the major therapeutic areas including, but not limited to, anti-infectives such as antibiotics and antiviral agents; analgesics and analgesic combinations; local and general anesthetics; anorexics; antiarthritics; antiasthmatic agents; anticonvulsants; antidepressants; antihistamines; anti-inflammatory agents; antinauseants; antimigrane agents; antineoplastics; antipruritics; antipsychotics; antipyretics; antispasmodics; cardiovascular preparations (including calcium channel blockers, beta-blockers, beta-agonists and antiarrythmics); antihypertensives; diuretics; vasodilators; central nervous system stimulants; cough and cold preparations; decongestants; diagnostics; hormones; bone growth stimulants and bone resorption inhibitors; immunosuppressives; muscle relaxants; psychostimulants; sedatives; tranquilizers; proteins, peptides, and fragments thereof (whether naturally occurring, chemically synthesized or recombinantly produced); and nucleic acid molecules (polymeric forms of two or more nucleotides, either ribonucleotides (RNA) or deoxyribonucleotides (DNA) including double- and single-stranded molecules and supercoiled or condensed molecules, gene constructs, expression vectors, plasmids, antisense molecules and the like).

Particles of a therapeutic agent, alone or in combination with other drugs or agents, are typically prepared as pharmaceutical compositions which can contain one or more added materials such as carriers, vehicles, and/or excipients. "Carriers," "vehicles" and "excipients" generally refer to substantially inert materials which are nontoxic and do not interact with other components of the composition in a deleterious manner. These materials can be used to increase the amount of solids in particulate pharmaceutical compositions. Examples of suitable carriers include silicone, gelatin, waxes, and like materials. Examples of normally employed "excipients," include pharmaceutical grades of dextrose, sucrose, lactose, trehalose, mannitol, sorbitol, inositol, dextran, starch, cellulose, sodium or calcium phosphates, calcium sulfate, citric acid, tartaric acid, glycine, high molecular weight polyethylene glycols (PEG), erodible polymers (such as polylactic acid, polyglycolic acid, and copolymers thereof), and combinations thereof. In addition, it may be desirable to include a charged lipid and/or detergent in the pharmaceutical compositions. Such materials can be used as stabilizers, anti-oxidants, or used to reduce the possibility of local irritation at the site of administration. Suitable charged lipids include, without limitation, phosphatidylcholines (lecithin), and the like. Detergents will typically be a nonionic, anionic, cationic or amphoteric surfactant. Examples of suitable surfactants include, for example, Tergitol® and Triton® surfactants (Union Carbide Chemicals and Plastics, Danbury, Conn.), polyoxyethylenesorbitans, e.g., TWEEN® surfactants (Atlas Chemical Industries, Wilmington, Del.), polyoxyethylene ethers, e.g., Brij, pharmaceutically acceptable fatty acid esters, e.g., lauryl sulfate and salts thereof (SDS), and like materials.

"Gene delivery" refers to methods or systems for reliably inserting foreign nucleotide sequences, either DNA or RNA, into a recipient's cells. Such methods can result in expression of non-integrated transferred nucleotide sequences, extrachromosomal replication and expression of transferred replicons (e.g., episomes), or integration of transferred genetic material into the genomic DNA of the recipient's cells.

By "vector" is meant any genetic element, such as a plasmid, phage, transposon, cosmid, chromosome, virus, virion, etc., which can transfer gene sequences between cells.

B. General Methods

In one embodiment of the invention, a needleless syringe is provided which has an elongate nozzle having a bend between the upstream and downstream termini thereof. The upstream terminus of the nozzle is, or is arranged to be, interfaced with a suitable energizing means that provides sufficient energetic force to deliver particles comprising a therapeutic agent from the syringe into target skin or mucosal tissue. The syringe has a release means for releasing an energetic force from the energizing means, thereby creating a supersonic condition within the nozzle.

One advantage provided by the present invention is that syringes of the type described in U.S. Pat. No. 5,630,796 generally have a straight nozzle portion that terminates with an outlet directed along the major axis of the nozzle. While such a configuration is suitable for injection directed to most target surfaces on a subject's body, some applications, e.g., dental applications, require that therapeutic agents be delivered into the gums or palate close to the teeth. Such injections can be very painful and cause distress both to the person delivering the injection and the subject. It is thus desirable to use a needleless injection device for delivery of therapeutics to mucosa such as tissue of the palate and other relatively inaccessible sites within the mouth. Further, it is desirable to provide a device that is easy to position within a working area of limited space, and to position the device for delivery to target surfaces with the axis of the nozzle substantially perpendicular to the target surface.

The present needleless syringe provides these features using the above-described nozzle configuration. The syringe, which comprises an elongate tubular nozzle having a bend near its downstream terminus can be connected to an energizing means such as a source of gaseous pressure. A release means is actuated to suddenly release a driving gas from the energizing means, thereby creating a supersonic condition within the nozzle. A source of particles comprising a therapeutic agent is arranged in the syringe such that they can be propelled from the downstream terminus of the nozzle upon release of the gas.

A number of alternative energizing means can be used with the present needleless syringe device. For example, a chamber containing a reservoir of compressed gas can be arranged at the upstream end of the nozzle. The gas can be released from the energizing chamber by way of a pierceable membrane or a valve, such as a spring-loaded ball valve, which is actuated by either mechanical means or by manual manipulation, for example, by movement of two parts of the syringe relative to each other. Alternatively, the energizing chamber can be fitted with means for providing a controlled build-up of gaseous pressure from an upstream or associated source. For example, release of a pressurized gas flow may be achieved by building up pressure behind a rupturable membrane until the pressure difference across the membrane is sufficient to rupture the membrane and release the gas suddenly into the nozzle. The velocity of the shockwave provided by the energizing means can be increased if the driving gas is lighter than air, e.g., helium. This effect can be enhanced if the nozzle is also initially filled with a volume of gas which also is lighter than air, e.g., helium.

The release means may thus comprise a rupturable membrane which initially closes the passageway through the nozzle, and a valve for releasing gas from a source of pressurized gas into a chamber behind the membrane until the membrane ruptures. Alternatively, the release means may be a self-opening valve having sufficiently fast action, such as a closure element which is initially held in a closed position, and means for releasing the element whereupon the element moves to an open position under the pressure of the gas source.

The nozzle of the syringe may be flexible, for example comprising a metal coil, and can also be embedded within a pliable material. In this manner, the bend in the nozzle can be adjusted over a range of desired angles, and remain stable in the adjusted position during operation of the device. This facilitates positioning of the downstream terminus of the nozzle adjacent to various otherwise inaccessible target surfaces, for example within a subject's mouth or other mucosal cavity.

Referring now to the accompanying drawings, FIG. 1 depicts a first embodiment of a needleless syringe that is suitable for delivering particles to a target surface. The syringe has an energizing means comprised of a cylindrical reservoir 3 initially containing helium under a pressure of between 40 and 100 bar, preferably about 80 bar. The reservoir, which can be provided as a separate item, is sealably coupled to, and in fluid communication with, a first opening of a body portion 4 which contains a rupture chamber, indicated at 5. Connection of the reservoir to the body portion can be facilitated by any suitable pressure-tight coupling. A second opening of the body portion 4 is sealably coupled to, and in fluid communication with, the head 6 of a nozzle portion 7. A sealed capsule 8 is sealably interposed between a flange on the body portion 4 and the end of the nozzle head 6. The capsule 8 is comprised of a pair of rupturable membranes, indicated at 9, that are spaced apart from each other at their edges by a ring to provide a concavity. The concavity houses particles P comprising a therapeutic agent which are to be delivered from the needleless syringe. The connections between the reservoir 3 and the body portion 4, and between the body portion 4 and the nozzle head 6 can comprise threaded connections or any other suitable attachment means, such as bayonet couplings or snap fittings.

The nozzle of the syringe, generally indicated at 7, has a substantially right-angular shape, and includes a bent portion 11, an upstream portion 10, and a downstream portion 12. The upstream portion 11 of the nozzle is longer and has a larger diameter relative to the shorter downstream portion 12. In addition, the downstream portion comprises a convergent/divergent shape. The nozzle terminates, at its downstream terminus, in a soft annular spacer 13 within which an exhaust passage 14 leads back along the nozzle 7 to exhaust ports 15 in the nozzle head 6.

In use, annular spacer 13 is placed in proximity to, or in contact with, the target skin or mucosal surface, a plunger 16 is depressed and a valve 17 actuated to an open position, allowing release of a driving gas, e.g., helium, from the reservoir 3 into a rupture chamber 5. The valve 17 is preferably a self-opening (and fast-acting) valve. When the pressure in the rupture chamber 5 has reached a sufficient value, the rupture membranes 9 burst, releasing a flow of gas which propagates through the nozzle 7 with the particles P entrained therewithin. The flow of gas and particles passes around the bend 11 and enters into the narrower portion 12 of the nozzle. The narrower portion has a convergent entry portion followed by a short cylindrical portion which leads to a larger, divergent portion of nozzle having a lesser angle of conicity than the convergent part. In so doing, the gas flow is accelerated to supersonic speed of Mach 2 to Mach 8 and the particles are carried by the gas out through the spacer 13 and into contact with the target surface. The gaseous shockwave, which is reflected from the target surface, passes back through the exhaust passage 14, whereby the energy of the shockwave can be dissipated with minimal noise.

Referring now to FIG. 2, a second embodiment of a needleless syringe is depicted. In this embodiment, release of a driving gas into a chamber 5 from a reservoir 3 enables the gas to flow through an elongate passageway 10 in the nozzle. A rupturable membrane 18, arranged in a downstream portion 19 of the nozzle allows the pressure provided by the released gas flow to build up behind a rupturable membrane in a chamber behind the membrane 18. The downstream portion 19 of the nozzle projects substantially laterally from the major axis of the elongate passageway 10. This downstream portion 19 contains a diaphragm 20 has an internal surface facing the rupturable membrane 18, and an external surface facing outwardly relative to the syringe. The diaphragm 20 is moveable between an initial position in which a concavity is provided on the external surface of the diaphragm, and a dynamic position in which the external surface of the diaphragm is substantially convex. This diaphragm configuration is described in commonly assigned U.S. patent application Ser. No. 08/860,403, filed Jun. 23, 1997 by Bellhouse et al. and entitled "Particle Delivery," which application is incorporated herein by reference.

The diaphragm 20 can be an eversible dome-shaped membrane that is comprised of any suitably resilient, flexible polymeric material which can withstand the impact of a shock wave provided by a gas flow travelling at a velocity at or approaching supersonic speed. Exemplary materials include, for example, a polyurethane or silicone rubber material. Selection of suitable flexible membranes is within the capabilities of the reasonably skilled artisan upon reading this specification. Alternatively, the diaphragm 20 can be a bistable membrane which is shaped in the form of a dome comprised of a resilient, polymeric material such as polyester (e.g., Mylar®). The bistable membrane can be formed by thermoforming in a suitable jig. The bistable membrane is moveable between an initial inverted position and a dynamic everted position.

Particles comprising a therapeutic agent will initially be provided in the concavity of the outwardly facing external surface of the diaphragm 20. The particles may be attached to the diaphragm by electrostatic forces, by their natural sticky nature, or by way of an adhesive agent, or by the adhesive effect provided by evaporation of water or ethanol in which the particles have been suspended. Particularly, the particles may be retained by a weak adhesive or cohesive agent which temporarily binds the particles to the external face of the diaphragm, and possibly also to each other. Exemplary adhesive/cohesive agents include, for example, water, ethanol, methanol, glycerol, KY jelly, sucrose solution, trehalose, silicone oil, albumin, and volatile granulation solvents, such as perfluoro alkanes, which are well known in the tabletting art.

Alternatively, the particles can be retained on the diaphragm by freezing. The freezing process can be slow, e.g., using a standard refrigerator, or rapid, using e.g., liquid nitrogen or dry ice. If the particles are hygroscopic, then the freezing process harnesses the moisture content in the particles in order to bond the particles to the diaphragm, and possibly also to each other. Upon thawing, the adhesion/cohesion can be maintained.

Furthermore, the particles may be attached to the diaphragm by way of compacting the particles within the concavity of the diaphragm using a suitable press. The particles and diaphragm assembly can likewise be placed in a centrifuge to allow centrifugal acceleration forces to adhere the particles to the exterior surface of the diaphragm. This compaction process "sticks" the particles to the diaphragm and produces an even distribution of particles.

The diaphragm 20 may, optionally, further comprise features on the concave side thereof, which features are useful for retaining the particles. For example, one or more annular rings, or a centrally disposed recess can be provided respectively on, or in, the external surface of the diaphragm.

In one particular embodiment, the particles disposed on the diaphragm 20 are covered by a thin barrier film which ruptures upon movement of the diaphragm to its dynamic position. The process of releasing the particles without shedding fragments of the barrier film can be aided by scoring, punching, cutting, or providing other lines of weakness in the barrier film. Further, the film may provide the sole means of retaining the particles in the concavity, or the film may be provided to maintain sterility with the particles being otherwise immobilized on the diaphragm.

Figure 5:
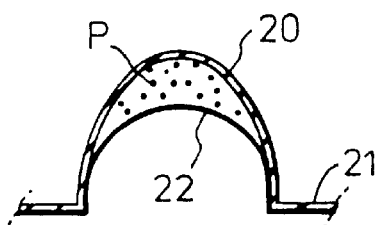
Figure 6:
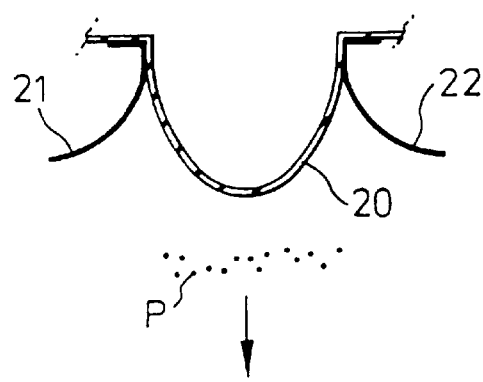

Referring now to FIGS. 2, 5 and 6, the diaphragm 20 has a peripheral flange 21. The concavity of the diaphragm initially contains particles P comprising a therapeutic agent which are retained to the diaphragm by one of the methods referred to above. A thin barrier film 22 is sealed at the edges thereof to the diaphragm 20. The downstream portion of the syringe is assembled by inserting the rupturable membrane 18 into a counterbore in the portion 19 such that its edges engage an annular shoulder at the end of the counterbore, inserting a spacer sleeve 23 so that it abuts the edge of the diaphragm, inserting the diaphragm as shown in FIG. 5, so that flange 21 engages the end of the spacer, and securing the three parts in place by attaching the assembly to the downstream terminus of the nozzle by way of a gland nut 24.

In operation, when the gaseous pressure released from the reservoir 3 has reached a sufficient value, the rupture membrane 18 bursts, releasing a shockwave which travels faster than the speed of sound (typically two or three times faster) and contacts the internal surface of the diaphragm 20. The impact of the gaseous shock wave upon the internal surface of the diaphragm provides sufficient force to suddenly impel the diaphragm from its initial position to a dynamic everted (outwardly convex) position as shown in FIG. 6, thereby dislodging the particles P comprising the therapeutic agent from the external surface of the diaphragm and propel them toward a target surface, simultaneously rupturing the barrier film 22. The particles are accelerated from the diaphragm at velocities sufficient for the transdermal delivery thereof across skin or mucosal tissue.

Referring now to FIG. 3, yet another embodiment of the invention is depicted. This particular embodiment is similar to the device of FIG. 2, except that the downstream portion of the nozzle is connected with the upstream portion of the nozzle through a smooth, curving bend, rather than through a sharp, angular bend. Also, the rupturable diaphragm 18 is positioned at the upstream end of the upstream portion of the nozzle, and closes off the outlet of a rupture chamber 5. The flange of the eversible diaphragm 20 is positioned in direct engagement with the shoulder at the end of the counterbore in the downstream portion of the nozzle, and is held in position by a sealing ring and a gland nut 25.

The device of FIG. 3 operates in substantially the same manner as the device of FIG. 2, with the notable exception that the supersonic shockwave is produced at the upstream end of the nozzle, e.g., upon rupture of the membrane 18, and travels along the majority of the nozzle before contacting the diaphragm 20 to cause expulsion of the particles P from the syringe device.

Figure 4:
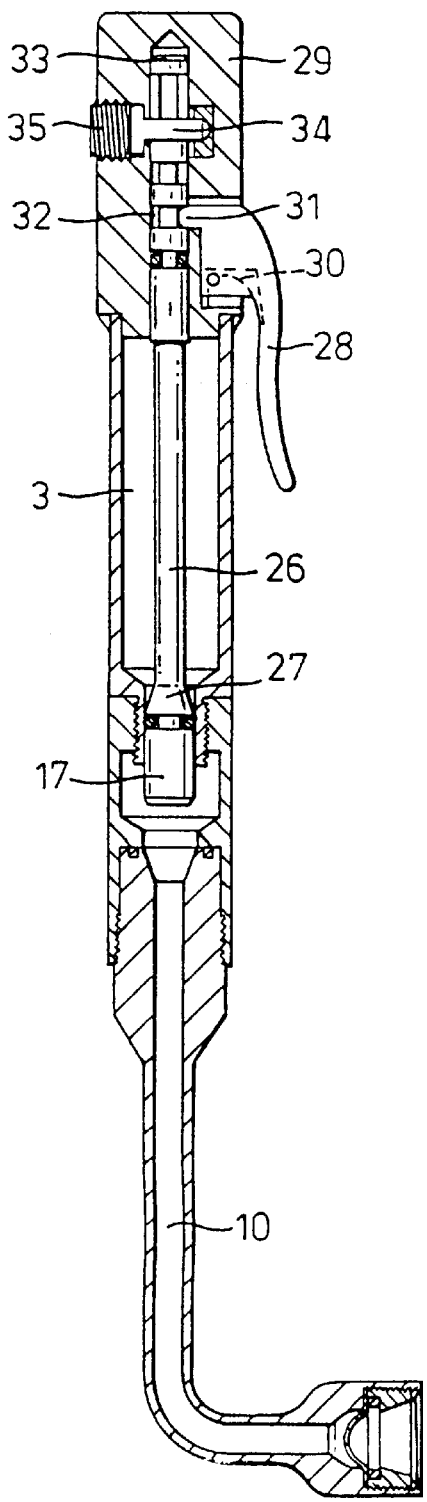

An even further embodiment of the invention is depicted in FIG. 4. In this embodiment, a release means comprises a valve operated by a valve stem 26 which carries a valve closure element 17 at its lower, downstream end. The closure element 17 is connected to the valve stem by way of a frusto conical portion 27. Since there is no equivalent enlarged portion at the upstream end of the valve stem 26, pressure in the reservoir 3, which acts on the portion 27 continually urges the stem 26 downwardly, and hence the element 17 is biased toward an open position. Movement of the stem to its open position is initially prevented by an actuation means 28, which is pivotally connected to a head 29 of the reservoir 3. The actuation means 28 is urged by a leaf spring 30 to rotate in an anti-clockwise direction as seen in FIG. 4, so that a tip 31 thereof engages an annular groove 32 in the upper part of the stem. When the actuation means is depressed and pivots clockwise, the tip 31 moves out of the groove 32, allowing the stem 26 to move suddenly downwardly under the high pressure in the reservoir 3, releasing a gas flow from the reservoir into the nozzle 10 to produce a supersonic shockwave which travels along the nozzle and everts the diaphragm 20. The downward movement of the stem 26 is limited by engagement of a flange 33, at the upper end of the stem, with the arms of a U-shaped yoke 34, which is inserted through a lateral bore in the head 29, the bore being closed by a screw threaded plug 35.

With respect to each of the above-described needleless syringe devices, the nozzles can be prefilled with a gas which is lighter than air, e.g., helium. Furthermore, gas provided by the energizing means may be helium at a pressure of about 40 to 80 bar.

The needleless syringes of the present invention can be used for delivery of powdered therapeutic compounds and compositions across skin or mucosal tissue, for delivery of genetic material into living cells (e.g., gene therapy or nucleic acid vaccination), both in vivo and ex vivo, and for the delivery of biopharmaceuticals to mucosa, skin, muscle, blood or lymph. The syringes can also be used in conjunction with surgery to deliver therapeutic agents, drugs, immunogens, and/or biologics to organ surfaces, solid tumors and/or to surgical cavities (e.g., tumor beds or cavities after tumor resection). In theory, practically any agent that can be prepared in a substantially solid, particulate form can be safely and easily delivered using the present devices.

Delivery of therapeutic agents from the above-described needleless syringe systems is generally practiced using particles having an approximate size generally ranging from 0.1 to 250 $\mu$m. For drug delivery, the optimal particle size is usually at least about 10 to 15 $\mu$m (the size of a typical cell). For gene delivery, the optimal particle size is generally substantially smaller than 10 $\mu$m. Particles larger than about 250 $\mu$m can also be delivered from the devices, with the upper limitation being the point at which the size of the particles would cause untoward damage to the skin cells. The actual distance which the delivered particles will penetrate a target surface depends upon particle size (e.g., the nominal particle diameter assuming a roughly spherical particle geometry), particle density, the initial velocity at which the particle impacts the surface, and the density and kinematic viscosity of the targeted skin or mucosal tissue. In this regard, optimal particle densities for use in needleless injection generally range between about 0.1 and 25 g/cm$^3$, preferably between about 0.9 and 1.5 g/cm$^3$, and injection velocities can range from about 200 to about 3,000 m/sec.

When nucleic acid preparations, e.g., DNA molecules, are to be delivered using the devices of the present invention, the preparations may optionally be encapsulated, adsorbed to, or associated with, carrier particles. Suitable carrier particles can be comprised of any high density, biologically inert material. Dense materials are preferred in order to provide particles that can be readily accelerated toward a target over a short distance, wherein the particles are still sufficiently small in size relative to the cells into which they are to be delivered.

In particular, tungsten, gold, platinum and iridium carrier particles can be used. Tungsten and gold particles are preferred. Tungsten particles are readily available in average sizes of 0.5 to 2.0 $\mu$m in diameter, and are thus suited for intracellular delivery. Gold is a preferred material since it has high density, is relatively inert to biological materials and resists oxidation, and is readily available in the form of spheres having an average diameter of from about 0.2 to 3 $\mu$m.

C. Experimental

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

EXAMPLE 1

Transmucosal Delivery of Testosterone

Testosterone and its derivatives have been given orally for the treatment of hypogonadal men (Niesschlag et al. (1976)

*Hormone Research* 7:138–145; Skakkebaek et al. (1981) *Clinical Endocrinol.* 14:49–61; and Gooren, L. (1986) *Intern, J. Androl.* 9:21–26). The "first-pass" effect limits the effectiveness of testosterone treatment when administered orally, where the testosterone is absorbed entering the hepatic circulation and immediately degraded by the liver (98% first pass degradation). Moreover, a major drawback of oral androgenic therapy compared to parenteral treatment is the exposure of the liver to high androgen loads, increasing the likelihood of undesirable effects on, for example, lipid metabolism (Conway et al., (1988) *Int. J. Androl.* 112:47–64; and Thompson et al., (1989) *JAMA* 261:1165–1168).

Thus, the following study was carried out to assess the transmucosal delivery of testosterone using a needleless syringe constructed in accordance with the present invention.

Testosterone (Sigma Chemicals) was milled and sieved into a particle size range (approximately 50–100 μm) suitable for transmucosal delivery from a needleless syringe using standard stainless steel mesh sieves. Female New Zealand White rabbit subjects weighing between 2.2–2.8 kg were used and allowed food and water ad libitum. The rabbits (n=8) were randomly assigned to one of two treatment groups. The first treatment group received testosterone (2.0 mg dose) as a suspension in 35% polyvinylpyrrolidone C-30 in water (6 mg/g testosterone concentration) via subcutaneous injection. The second treatment group received testosterone (2.0 mg dose of testosterone particles ranging from 53–75 μm) as two 1.0 mg transmucosal administrations from an OralJect™ needleless syringe device abutted against the cheek mucosa.

Whole blood (1.0 ml) was taken at times 0, 0.5, 1, 2, 4, 6, 8, 12, 24 and 48 hours, the serum aspirated and assayed for testosterone by radioimmunoassay (DPC). The OralJect™ device is a prototype device of the present invention that is actuated by helium at 40 bar.

The results of the study are depicted below in Table 1 which shows the mean results and ranges for each treatment group from the study. As can be seen, testosterone bioavailability in the order of 48.3% was achieved following OralJect™ transmucosal delivery with a $t_{max}$ of 30 minutes in all animals. $C_{max}$ (the mean maximum serum concentration) was not significantly different between treatments although there was a tendency for it to be lower following OralJect™ administration. A second minor peak of serum testosterone was evident at 12 hours post administration suggesting a possible depot effect following transmucosal delivery of testosterone by the OralJect™ device.

TABLE 1

| Treatment | Subcutaneous | OralJect ™ |
|---|---|---|
| $C_{max}$ nmol/l | 34.8 ± 6.9 | 25.5 ± 3.5 |
| $C_{max}$ range nmol/l | 26.9–55.2 | 177–33.5 |
| % BA† | NA | 48.3 |

†% bioavailability

These data demonstrate that it is possible to deliver a hydrophobic drug such as testosterone transmucosally using the device of the present invention. The pharmacokinetic profile observed for such delivery was markedly different from that achieved following subcutaneous administration of the same formulation of testosterone.

EXAMPLE 2

Delivery of a Powdered Local Anaesthetic to Oral Mucosa using a Needleless Syringe Device The following studies were carried out to assess the effectiveness of transmucosal delivery to oral mucosa using a device constructed in accordance with the present invention, to provide a comparison between such delivery and a conventional needle-syringe injection, and to assess the anaesthetic effect provided by transmucosal delivery.

A randomized, double-blind, negatively controlled study was carried out in normal, healthy human subjects as follows. Initially, a single 3 mg dose of lignocaine HCL particles sized between 38 and 53 μm was delivered from a needleless syringe constructed in accordance with the invention. The lignocaine was delivered to the oral mucosa adjacent to the number 12 and 22 lateral incisors in 14 trial subjects. The delivery sites were then visually assessed for evidence of damage or irritation to the mucosal tissues. In all subjects, no evidence of any tissue reaction was observed 24–48 hours after delivery.

In a second study, a single 3.0 mg dose of lignocaine HCL particles (as above) was delivered using a needleless syringe, and a single 0.2 mL dose of 2% lignocaine HCL was delivered via needle-syringe injection. Pain associated with the administration of each treatment was scored in all 14 subjects using a 100 mm visual analogue scale immediately after each treatment, wherein 100% indicates a painful treatment, and 0% indicates a pain-free treatment. The needleless syringe employed in the study was operated using 40 bar helium driving gas to expel anaesthetic particles from a flexible, eversible dome-shaped membrane comprised of a 400 μm, 6 mm polyurethane film. The mean values of all 14 scores were: 2.4% for the needleless syringe-based procedure, and 49.9% for the needle-syringe injection, indicating that the delivery methods of the present invention are virtually painless relative to conventional injection techniques.

A randomized, double-blind study was then carried out as follows. Treatments were given to 14 subjects over the course of three visits. The treatments provided to the subjects in each visit were either a single 3.0 mg dose of Lignocaine HCL particles from the above-described needleless syringe device, or 0.0 mg (as a blinded negative control). Accordingly, treatments provided over the course of the three visits were either: two actual (3.0 mg) doses of the anaesthetic particles and one placebo; or two placebos and one actual (3.0 mg) dose. Pain stimulus was provided by probing oral mucosa with the back of a 27G dental needle, wherein the probe sequence was a probe on an untreated area of the mucosa, and then a probe on the treated area of the mucosa 1 minute post delivery. Again, the pain associated with the probe of the untreated and treated areas was scored on visual analogue scales using the above scoring methods immediately after each probe.

The mean values of all pain response scores were: 55.6% for the control (untreated) probe; 30.6% for the placebo treated probe; and 15.0% for the actual treated probe. These results demonstrate a superior level of local anaesthesia relative to the placebo treatments.

Accordingly, novel needleless syringe delivery systems and methods for using the same are disclosed. Although preferred embodiments of the subject invention have been described in some detail, it is understood that obvious variations can be made without departing from the spirit and the scope of the invention as defined by the appended claims.

We claim:

1. A needleless syringe for delivering particles comprising a therapeutic agent across skin or mucosal tissue of a vertebrate subject, said syringe comprising:

(a) an elongate tubular nozzle having an upstream terminus and a downstream terminus and a bend between said upstream and downstream termini, wherein the upstream terminus is capable of interfacing with an energizing means; and (b) release means associated with the nozzle for releasing into the upstream terminus of the nozzle an energetic force from the energizing means to create a supersonic condition within the nozzle.

2. The syringe of claim 1, wherein the upstream terminus of the nozzle is interfaced with a source of pressurized gas.

3. The syringe of claim 2, wherein the source of pressurized gas comprises a gas canister containing a releasable volume of a driving gas.

4. The syringe of claim 2, wherein the source of pressurized gas contains a gas which is lighter than air.

5. The syringe of claim 4, wherein the nozzle contains a volume of gas that is lighter than air.

6. The syringe of claim 2 further comprising valve means capable of actuation to release a volume of gas from the source of pressurized gas to create a gaseous shock wave within the nozzle.

7. The syringe of claim 6, wherein the release means comprises a rupturable membrane arranged within and closing the nozzle, whereby the released gas is temporarily retained in a chamber behind said membrane prior to the rupture thereof.

8. The syringe of claim 1, wherein the release means is a self-opening valve.

9. The syringe of claim 1, wherein the nozzle contains a volume of gas that is lighter than air.

10. The syringe of claim 1, wherein the supersonic condition within the nozzle is a supersonic gas flow.

11. The syringe of claim 10, wherein the nozzle diameter between the bend and the downstream terminus is smaller than the nozzle diameter between the upstream terminus and the bend, whereby the supersonic gas flow is attained in the nozzle only between the bend and the downstream terminus.

12. The syringe of claim 11, wherein the portion of the nozzle between the bend and the downstream terminus has a convergent portion.

13. The syringe of claim 1 further comprising an upstream and a downstream rupturable membrane that extend across the interior of the nozzle, wherein particles comprising a therapeutic agent are housed in the nozzle between said rupturable membranes.

14. The syringe of claim 13, wherein the release means comprises the upstream or downstream rupturable membrane.

15. The syringe of claim 1 further comprising a diaphragm arranged adjacent to the downstream terminus of the nozzle, said diaphragm having an internal surface facing the interior of the nozzle and an external surface, wherein said diaphragm is moveable between an initial position in which a concavity is provided on the external surface of the diaphragm, and a dynamic position in which the external surface of the diaphragm is substantially convex.

16. The syringe of claim 15, wherein the diaphragm is an eversible dome-shaped membrane comprised of a flexible polymeric material.

17. The syringe of claim 15, wherein the diaphragm is a bistable membrane that is moveable between an initial inverted position and a dynamic everted position.

18. The syringe of claim 15 further comprising particles comprising a therapeutic agent housed within the concavity in the external surface of the diaphragm.

19. The syringe of claim 1, wherein the nozzle is flexible such that the bend in the nozzle can be adjusted over a range of angles.

20. A method for delivering particles comprising a therapeutic agent to skin or mucosal tissue, said method comprising:

(a) providing the needleless syringe of claim 1 interfaced with an energizing means;

(b) loading said needleless syringe with particles comprising a therapeutic agent;

(c) positioning the downstream terminus of the nozzle of said syringe adjacent to the skin or mucosal tissue; and (d) actuating the release means to create a supersonic condition within the nozzle, thereby accelerating said particles into the skin or mucosal tissue.

21. The method of claim 20, wherein the particles are accelerated toward the skin or mucosal tissue at a velocity of about 200 to 2,500 m/sec.

22. The method of claim 20, wherein the particles have a size predominantly in the range of about 10 to 40 $\mu$m.

23. The method of claim 20, wherein the particles have a density in the range of 0.5 to 2 g/cm$^3$.

24. The method of claim 20, wherein the particles are accelerated from the downstream terminus of the nozzle at a momentum density between 4 and 7 kg/sec/m.

25. The method of claim 20, wherein the therapeutic agent is a topically active local anaesthetic.

26. The method of claim 25, wherein the local anaesthetic is selected from the group consisting of lignocaine hydrochloride, lignocaine base, ropivacaine hydrochloride, bupivacaine, procaine, prilocaine, tetracaine, etidocaine, and benzocaine.

27. The method of claim 25, wherein the local anaesthetic is mixed with epinephrine.

28. The method of claim 20, wherein the therapeutic agent is selected from the group consisting of a systemically-active organic small molecule, an inorganic small molecule, a peptide, a protein, a vaccine, an oligonucleotide, and a metal ion.

29. The method of claim 28, wherein the therapeutic agent is selected from the group consisting of insulin, testosterone, growth hormone, glucagon, atropine, alprazolam, calcitonin, desmopressin, 5HT, dihydroergotamine, and interleukin.

30. The method of claim 20, wherein the particles are delivered to a mucosal surface.

31. The method of claim 30, wherein the particles are delivered to a mucosal surface selected from the group consisting of gum mucosa, cheek mucosa, palate mucosa, vaginal mucosa, rectal mucosa, nasal mucosa, and ocular mucosa.

* * * * *